United States Patent
Zhang et al.

(10) Patent No.: US 7,157,477 B2
(45) Date of Patent: Jan. 2, 2007

(54) ALIPHATIC AMINO-SUBSTITUTED DEMETHOXYLATED HYPOCRELLINS AND THEIR SYNTHESIS

(75) Inventors: Manhua Zhang, Beijing (CN); Shangjie Xu, Beijing (CN); Tao Wu, Beijing (CN); Shen Chen, Beijing (CN); Tao Shen, Beijing (CN)

(73) Assignees: Altachem Pharma Ltd., Alberta (CA); Institute of Photographic Chemistry Academia Sinica, Beijing (CN)

( * ) Notice: Subject to any disclaimer, the term of this patent is extended or adjusted under 35 U.S.C. 154(b) by 98 days.

(21) Appl. No.: 10/415,249

(22) PCT Filed: Oct. 24, 2001

(86) PCT No.: PCT/IB01/01993

§ 371 (c)(1),
(2), (4) Date: Aug. 26, 2003

(87) PCT Pub. No.: WO02/34708

PCT Pub. Date: May 2, 2002

(65) Prior Publication Data

US 2004/0092557 A1    May 13, 2004

(30) Foreign Application Priority Data

Oct. 25, 2000    (CN) .............................. 00130048 A

(51) Int. Cl.
*C07D 213/38*    (2006.01)
*C07C 225/32*    (2006.01)
*A61K 31/135*    (2006.01)
*A61K 31/44*    (2006.01)

(52) U.S. Cl. ..................... 514/357; 514/656; 514/661; 514/680; 546/285; 552/284

(58) Field of Classification Search .......... 546/285; 548/300.4, 504, 528; 549/77; 552/284; 514/357, 656, 661, 680
See application file for complete search history.

(56) References Cited

U.S. PATENT DOCUMENTS 6,627,664 B1 *    9/2003    Miller et al. ................ 514/680
2004/0110846 A1 *    6/2004    Leveugle ..................... 514/856

FOREIGN PATENT DOCUMENTS

CN    1194263    9/1998

OTHER PUBLICATIONS

Diwu et al., Anti-Cancer Drug Design, 8, 129-143, 1993.*
Miller et al., Photochemistry and Photobiologyk 65(4), 714-722, 1997.*
Zhang et al., Journal of Photochemistry and Photobiology, B: Biology, 44(1), 21-28, 1998.*
Wu et al., Anti-Cancer Drug Design, 15(4), 287-293, 2000.*
Zhang et al., Chemical Abstracts, 132:279061, 2000.*
Wu et al., Chinese Chemical Letters, 11(11), 963-966, Nov. 2000.*
Wu et al., Anti-Cancer Drug Design, 15, 287-293, Feb. 24, 2000.*
Zhang, et al., "Amino Substituted Demethoxy Hypocrellin, Preparing Method", Abstract in English from CN 1194263A.
Jiang, et al., "2-Mercapto-Ethylamine Cyclized Hypocrell Preparation Process and Usage Thereof", Abstract in English from CN 1266061A.

* cited by examiner

Primary Examiner—Fiona T. Powers
(74) Attorney, Agent, or Firm—Christine C. O'Day; Edwards Angell Palmer & Dodge LLP

(57) ABSTRACT

The invention involves a methods and compositions for use in photodynamic therapy. Novel perylenequinone derivatives, conjugates comprising perylenequinone derivatives and a binding agent, and methods of treatment using these compositions are disclosed. The present invention relates to the field of photosensitizers possessing photodynamic activities. They possess high photodynamic activities and low dark toxicities, which makes them as more potent photodynamic agents than HPD against cancer and AIDS virus.

13 Claims, 4 Drawing Sheets

ALIPHATIC AMINO-SUBSTITUTED DEMETHOXYLATED HYPOCRELLINS AND THEIR SYNTHESIS

TECHNICAL FIELD

This patent discloses a new type of photosensitizers possessing photodynamic activities, i.e. aliphatic amino-substituted demethoxylated hypocrellins and their synthesis.

BACKGROUND ART

Photodynamic therapy (PDT) is a medical treatment that employs a combination of light and a photosensitizing agent to generate a cytotoxic effect of cancerous or other unwanted tissues. It possesses high effectiveness and safety compared with the conventional chemotherapy. The widely accepted PDT mechanism is that upon irradiation, the photosensitizer successively generates active oxygen species of high reactivity that the target molecules. Contrast with the traditional chemical medicine which can only kill one target molecule at a time, the PDT possesses remarkable high-effectiveness. On the other hand, the PDT has dual selectivity including drug-orientation and light-orientation, which avoids or decreases the damage to normal tissues, and increases the drug safety. This is important for cancer and AIDS treatments.

Photodynamic therapy (PDT) consists of introducing a photoactive drug into the body and subsequent illumination of tumor tissue by visible or near infrared light. In the presence of oxygen, illumination activates the drug and in turn produces reactive oxygen species leading to tissue damage. Owing to its advantages such as its relative selectivity in most sites, its compatibility with other treatment, its repeatability, its ease of delivery etc., PDT is slowly finding its place as a useful cancer treatment for certain types of cancers or clinical situation, such as early stage cancers of the lung, esophagus, stomach, cervix and cervical dysplasia, etc. [1].

With the rapid development of laser and optical-fiber techniques, the issue of light source in PDT is being resolved. The selection of the photosensitizer in PDT treatment becomes more critical. At present, the most popular photodynamic agent, photofrin, shows distinct curative effect on treating inchoate cancer, such as vesical, pulmonary and gastric cancers etc. Lipson et. al. employed hematoporphrin derivatives (HPD) to detect and control the cancer growing, and to treat galactophore cancer for the first time in 1966. Kelly and Snell reported that HPD had obviously photodynamic curative effect on the vesical cancer in Journal of Urology (1976, 115, 150). Dougherty et. al. reported that they used HPD as photosensitizer to study their photodynamic activities against thousands of cases of cerebric, jugular and ocular cancers etc. in Journal of NATO Cancer Institute (1975, 55, 115), and obvious curative effects are obtained. In 1978, Dougherty used HPD as photosensitizer to treat malignant cutaneous cancer and subcutaneous tumor, indicating that 111 pathological changes are cured completely or partially among 113 pathological changes. Porphyrin sensitizer is a π-conjugated system composed by four pyrrole rings and four methylene bridges, HPD and dihematoporphyrin ether or ester (DHE) is the comprehensive agent used in clinical therapy. When HPD is up to certain concentration, aggregation occurred readily in vitro and in vivo, which decreased the photodynamic activities of HPD. In Cell Biochemistry Function (1985, 3, 15), El-Far et al. reported the HPD are lipophilic and exhibited a certain extent of cancer cells-localization ability. They can be enriched selectively in cancer tissues, and the localization action and photosensitized activities are dependent on their hydrophobicility, aggregation and charge distributing.

To date, only Photofrin® has been approved by health boards in Canada, Japan, the Netherlands and the United States [2]. In spite of the favorable results obtained with Photofrin, some important factors still limit the efficacy of PDT, including its complex composition, the low extinction coefficient in the red spectral region and the prolonged cutaneous phototoxicity [3]. This is undoubtedly encouraging the search for more ideally suited photosensitizers.

Although the PDT using HPD as photosensitizers had received great attention, there are still some serious disadvantageous, i.e. complicated components, little absorption in the photodynamic window (600–900 nm), slow metabolism, toxicity and side-effect.

To overcome these limitations, all kinds of new photosensitizers are explored in recent years. The naturally occurring polycyclic quinones, hypocrellins, isolated from the fungus *hypocrella bambuase* (B. Et Br) *sacc*, grew abundantly in the southwestern part of China. Their high content (3–4%) in the fungus and easy separation and purification had received most attentions in the passed 20 years.

Hypocrellins derive their name from *Hypocrella bambusae sacc.*, a parasitic fungus of the Sinarundinaria species, which grows abundantly in the northwestern region of the Yunnan Province (People's Republic of China), the southeastern region of Tibet, and certain parts of Sri Lanka. Hypocrellins belong to the general class of perylenequinoid (PQP) pigments, and include hypocrellin A (HA) and hypocrellin B (HB).

In China some hospitals had used hypocrellins as photodynamic agent to treat certain dermatosis, such as pudendum bleaching, vitiligo and psoriasis. In 1980, Xiang-yi Wan and Zi-hua Luo reported that hypocrellin could be used to treat pudendum bleaching and cutaneous blotch in Kexue Tongbao (1980, 25, 1148) (in Chinese) and Yunnan Yiyao (1980, 1, 20) (in Chinese), respectively. Hypocrellin is used gradually to treat lichenification, vitiligo, and psoriasis and scald head. Yuan-teng Chen et al. identified one of the effective components, hypocrellin A (HA), in Liebigs Ann. Chem. (1981, 1880). Manhua Zhang and Li Liang et al. identified the other effective component of hypocrellin, hypocrellin B (HB) in Kexue Tongbao (1988, 33, 518) (in Chinese). Manhua Zhang et al. have studied the structures, photochemistry, photophysics, photobiology and cytology of hypocrellins for more than ten years. We observed that hypocrellins consisted of HA {3,10-dihydroxyl-4,9-dione-1,12-(2'-hydroxyl-2'-methyl-3'-actyl)propilidene(1',3')-2,6,7,11-tetramethoxyl-perylene} (see structure I) and HB {3,10-dihydroxyl-4,9-dione-1,12-(2'-methyl-3'-actyl-2',3'-dehydro)propilidene(1',3')-2,6,7,11-tetramethoxyl-perylene} (see structure II).

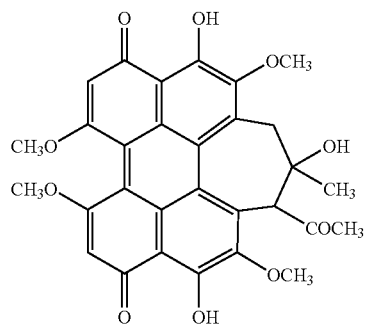

I

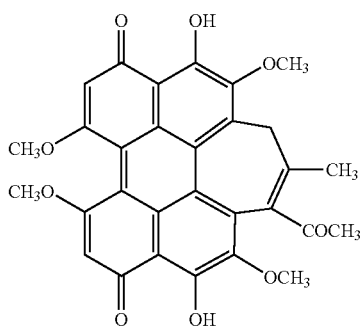

II

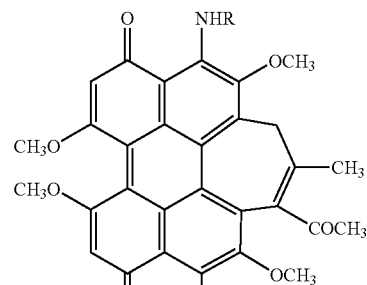

III

IV

As a new kind of photosensitizers, they possess several advantages, including easy preparation and purification, low toxicity, high stability, no aggregation, rapid metabolism, low side effect and selective localization in cancer tissues. These properties make them as promising second-generation photosensitizers. Lown et. al. reported that HB possessed distinct anti-AIDS action in Photochemistry and Photobiology (1997, 65, 352). However their little absorption in the photodynamic window limits their application in PDT. Hypocrellins, owing to their pure composition, favorable red light, absorption spectra, high quantum yields of singlet oxygen and facility for side-directed chemical modification, have been selected as potential photosensitizers for PDT [4]. A lot of derivatives of the parent hypocrellin B (HB) have been synthesized and studied. Some of them have shown promising anticancer properties (5–11). To overcome these limitations, lots of structural modifications of hypocrellins have been made. In 1994–1995, we and Lown prepared amino-substituted hypocrellins at about the same time. The amino-substituted hypocrellins exhibited strong absorption in the photodynamic window. With the aid of laser, they showed much higher photodynamic activities than their parent hypocrellins. Lown reported the photodamage to cancer cells by amino-substituted hypocrellins in detail in Photochemistry and Photobiology (1997, 65, 714). The original peri-hydroxylated perylenequinone structure of hypocrellins is altered in the amino-substituted derivatives prepared by Dr. Lown (see structures III and IV, the parent compounds of III and IV are isomers), which changed the photoactive position of hypocrellins. The method of amino-substituted HB reported by Lown is undesirable due to the numerous steps.

Manhua Zhang et al. reported that the mercapto-substituted hypocrellins exhibit little absorption in the photodynamic window due to the undesirable photoactive position.

DESCRIPTION OF THE FIGURES

FIG. 4A shows untreated control cells; FIG. 4B, dark control cells (light dose=0); and FIG. 4C, 24 hours post-irradiation.

FIG. 6A shows 2-BA-2-DMHB incubation; FIG. 6B, six hours after 2-BA-2-DMHB photosensitization at $LD_{90}$; FIG. 6C, HB incubation alone; and FIG. 6D, 24 hours after HB photosensitization at $LD_{90}$.

DISCLOSURE OF INVENTION

Figure 1:
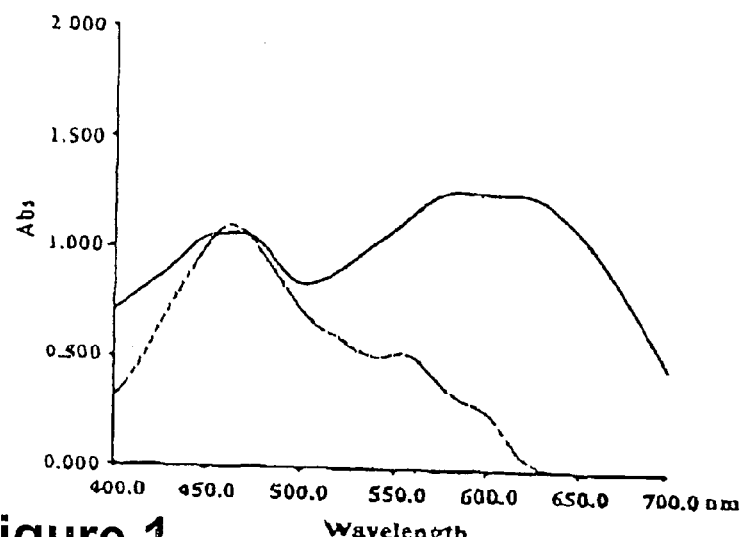
FIG. 1 shows the absorption data for HB and 2-BA-2-DMHB.

The present invention provides a new kind of aliphatic amino (containing alicyclic and aromatic ring)-substituted demethoxylated hypocrellins and their preparation method. These hypocrellin derivatives showed strong absorption in the photodynamic window, preserved the photodynamic properties of perihydroxylated perylenequinone structure. Upon irradiation with laser light, they can generate active oxygen species, including singlet oxygen ($^1O_2$), superoxide anion radical ($O_2^-$) and hydroxyl radical (HO·), and possess high photodynamic activity. They can be used to treat cancer and anti-AIDS virus.

The hypocrellin derivatives in the present invention consist of amino-substituted demethoxylated hypocrellins A and B, whose structures are shown as V and VI:

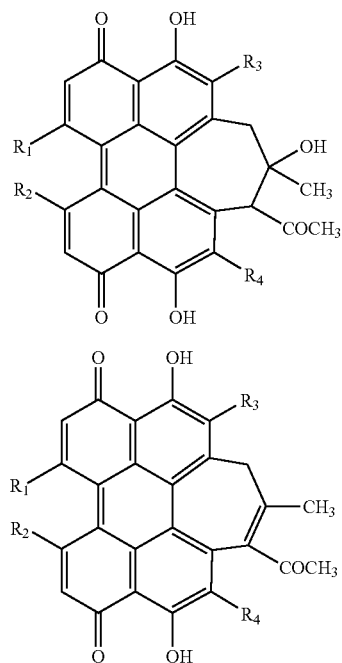

where $R_1$, $R_2$, $R_3$, $R_4$ are $OCH_3$ or $NHCH_2Ar$ (Ar are phenyl or pyridyl group), $NHCH(CH_2)$, (where $—CH(CH_2)_n$ are alicyclic group and n=3,4,5,6). 2-BA-2-DMHB is where $R_1$, $R_2$, $R_3$ are $OCH_3$, and $R_4$ is $NH(CH_2)_3CH_3$. Alternatively, $R_1$, $R_2$, $R_3$, $R_4$ may be $OCH_3$ or $NHCH_2(CH_2)_nAr$, wherein Ar is a phenyl, naphthyl, polycyclic aromatic or a heterocyclic moiety, and n is 0–12.

A hypocrellin derivative of the present invention also includes 2-butylamino-2-demethoxy-hypocrellin B (2-BA-2-DMHB). 2-BA-2-DMHB exhibits strong absorption in the red spectral region. Compared with its parent compound HB its absorption bands extended toward longer wavelengths. The extinction coefficient (6) at 583 nm was 2.5-fold as much as HB at 548 nm, and at 621 nm was over 3.8-fold as much as HB at 580 nm (Table 1). This will be more favorable to tissue penetration of clinically used light. 2-BA-2-DMHB has excellent photopotentiation of cellular damage. The MTT calorimetric assay results showed that 2-BA-2-DMHB didn't evoke 50% lethality even at the highest concentration tested (100 µM). This meant that the $LD_{50}$ in the dark of 2-BA-2-DMHB was more than 100 µM, which is comparable to that of any HB derivative reported previously [8–10], However, HB evoked 50% lethality at about 20 µM. In other words, the cytotoxicity of 2-BA-2-DMHB was much lower than that of HB. On the other hand, at a light dose of 24 Jcm$^{-2}$, the $LD_{50}$ of 2-BA-2-DMHB was about 0.4 µM, while that of HB was 2 µM. So 2-BA-2-DMHB showed over 25-fold photopotentiation as mush as HB in vitro, which would provide a wide safety margin for drug administration.

The hypocrellin derivatives of the present invention may also be conjugated to binding agents that bind pre-determined cells or structures in vitro or in vivo. Conjugation with monoclonal antibodies (e.g., immunoconjugates) affords specificity with respect to the treatment of a variety of diseases, including ovarian cancer and breast cancer. Fluorescence properties of the hypocrellins, or the fact that they are strongly colored, facilitates their use in the diagnosis of tumors and metastatic disease, and their spectral fingerprint facilitates differentiation between malignant, normal, inflamed, or physically damaged tissues. Further, these fluorescence properties can be detected through a variety of optical detection means.

Conjugation with monoclonal antibodies also affords a high degree of phototherapeutic specificity for a variety of diseases, including ovarian and breast cancer. The conjugates mediate phototoxicity through apoptotic cell death, primarily through type II photochemical reactions with intracellular and membrane targets. In the total absence of oxygen, phototoxicity is mediated through the type I photochemical reaction, a characteristic that is critical to the management of hypoxic tumor cells. They retain significant phototoxicity at 688 nm, well within the phototherapeutic window [Estey, et al., *Cancer Chemother. Pharmacol.*, 37:343 (1996)].

The present invention comprises the use of perylenequinone (PQP) derivatives as photodynamic agents, and the use of hypocrellin derivatives in photodynamic therapy (PDT).

The present invention also comprises a method of treating a disease by administering a therapeutically sufficient amount of at least one hypocrellin derivative of the present invention, and photoactivating the derivative(s). Typically, the hypocrellin derivative may be activated by exposing the derivative to a pre-determined wavelength of light.

The present invention also comprises a method of photodynamic treatment comprising administering a composition comprising one or more hypocrellin compounds of the present invention.

The invention also includes a method of treating cancer that is enhanced in the presence of light wavelengths between about 400 nm and about 850 nm. The invention also comprises using one or more PQP derivatives to generate singlet oxygen and a variety of toxic free radicals. Typically, compounds that are capable of generating singlet oxygen and/or toxic free radicals may be used to treat certain diseases and the like.

The invention also comprises using the hypocrellin derivatives that have anti-cancer and/or anti-viral activity, and enhancing the activity of these derivatives by photoactivating the derivative. The invention also includes using the hypocrellin derivatives to preferentially destroy or preferentially target cancer cells.

The invention also comprises a method for producing native perylenequinones, such as hypocrellin, synthesizing perylenequinone derivatives, such as hypocrellin A and hypocrellin B, radiolabeled hypocrellin B and radiolabeled hypocrellin B derivatives. The invention also comprises compositions containing perylenequinone derivatives, hypocrellin derivatives, radiolabeled hypocrellin B and radiolabeled hypocrellin B derivatives, perylenequinone conjugates, and hypocrellin conjugates.

The invention also comprises conjugating the PQP derivatives of the present invention to one or more binding agents, such as antibodies or an antibody fragment. The invention also comprises the PQP derivative conjugated to one or more binding agents, such as an antibody or antibody fragments. The invention also comprises conjugating the PQP derivatives, e.g., hypocrellin derivatives, to bNA minor-groove-binding agents to effect phototoxicity in a cell structure, such as the cell nucleus.

As used herein, a perylenequinone derivative or derivative refers to all demethoxylated compounds derived from native or natural perylenequinones and which can be activated by light of a pre-determined wavelength. In a preferred embodiment of the invention, the derivative is a compound derived from naturally occurring hypocrellin A or hypocrellin B, and hypocrellin-like compounds. Hypocrellin derivatives, as used herein, may be activated by light, and may be used as photodynamic agents. A derivative according to the invention may also be complexed with or include other active reagents, including but not limited to chemotherapeutic agents or alkylating agents.

The compounds of the present invention may be produced by any method that results in a purified or substantially purified compound, or in a compound that is useful as a photodynamic agent. The compounds of the present invention may also form a composition comprising a cocktail of compounds, e.g., more than one compound. These methods are well known in the art, e.g., Liu, et al., "Synthetic studies in novel hypocrellin B derivatives, Tetrahedron, 49:10785 (1993); and Diwu, et al., Anti-Cancer Drug Design, 8:129–143 (1993). Hypocrellin derivatives may be readily synthesized from the parent compound, hypocrellin B (HB), a natural product of the fungus *Hypocrella bambusae sacc.*, a phytopathogen of bamboo. The compounds of the present invention may also be produced synthetically as shown below. Exemplary methods of producing the compounds are also shown in more detail in the Examples. It is intended that the invention is not to be limited by the method of producing, isolating, or purifying the hypocrellin derivatives.

The preparation method of the hypocrellin derivatives in the present invention is described as follows: a hypocrellin, such as hypocrellin A or B, is dissolved in fresh distilled solvent containing excessive aliphatic amine and the resulting solution is stirred for 6–24 hours. The solvent is removed under reduced pressure. Chloroform is used to wash the residue for 34 times, and the chloroform layer is washed with water for 3–4 times. Chloroform is evaporated, then thin-layer chromatography (TLC) is used to separate the residue using 3:1:0.5 (V:V:V) cyclohexane-ethyl acetate-95% ethanol as eluent. The TLC purification is repeated twice, the pure amino-substituted demethoxylated hypocrellins are obtained. For the reaction, both hypocrellin A and B are used.

Aliphatic amines may include but are not limited to cyclopentylamine, cyclohexylamine, benzylamine, 3-pyridyl-methylamine and 4-pyridyl-methylamine. Amines may also include cyclobutylamine, histamine, 2-thiophenemethylamine, 2-pyrrolmethylamine, or tryptamine.

Solvents may include, but are not limited to benzene, pyridine, cyclohexane or 1,4-dioxane. Solvents may also include chlorobenzene, toluene, hexanes, petroleum ether, tetrahydrofuran, or N,N-dimethylformamide.

The hypocrellin derivatives in the present invention showed strong absorption in the photodynamic window (600–900 nm). Upon irradiation with laser light, they can generate active oxygen species, including singlet oxygen ($^1O_2$), superoxide anion radical ($O_2^-$) and hydroxyl radical (HO·). They possess several advantages, i.e., high photodynamic activities and low dark toxicity, which makes them as promising anti-cancer and anti-AIDS agents.

The studies on the photochemistry and photophysics of this kind of amino-substituted demethoxylated hypocrellin derivatives in the present invention suggested that they preserved the photoactive positions (as their parent hypocrellins), could effectively generate active oxygen species such as singlet oxygen ($^1O_2$) (the quantum yields of $^1O_2$ are 0.5–0.8, which are comparable with HA, HB and HPD) and superoxide anion radical ($O_2^-$) (the quantum yields of $O_2^-$ for amino-substituted demethoxylated hypocrellin derivatives are 2–5 times more than HB). They exhibited strong absorption in the photodynamic window (their extinction coefficients in the photodynamic window are 10–100 times more than HA, HB and HPD). All these results indicate that the amino-substituted demethoxylated hypocrellin derivatives in the present invention possess desirable activities as a new generation of photosensitizers.

The previous animal experiments showed that hypocrellin A and B have low toxicity. Lown's group has proved that the introduction of amino group enhanced the basicity of hypocrellins, which makes their preferable localization in lysosomes. The photodamage in lysosomes can induce the cancer cell degradation.

The amino-substituted hypocrellins in the present invention exhibit strong absorption in the photodynamic window ($\lambda_{max} > 10^4$ L·mol$^{-1}$·cm$^{-1}$), high quantum yield of singlet oxygen (comparable with their parent hypocrellins), high activity of charge transfer (the oxidation potential reduced to 0.8 V from 1.3 V, the quantum yield of $O_2^-$ generation is 3 times more than the parent hypocrellins), indicating that they possessed strong photodynamic action. The preparation method provided in the present invention is simple, mild, and low-cost can be easily scaled up.

Here another novel hypocrellin congener, 2-butylamino-2-demethoxy. hypocrellin B (2-BA-2-DMHB) [12], is found to be an effective photosensitizer. Its phototoxicity to HeLa cells and the initiation of apoptosis with it are reported.

As used herein, administering refers to any action that results in exposing or contacting one or more hypocrellin derivatives of the present invention with a pre-determined cell, cells, or tissue, typically mammalian. As used herein, administering may be conducted in vivo, in vitro, or ex vivo. For example, a composition may be administered by injection or through an endoscope. Administering also includes the direct application to cells of a composition according to the present invention. For example, during the course of surgery, tumor cells may be exposed. In accordance with an embodiment of the invention, these exposed cells (or tumors) may be exposed directly to a composition of the present invention, e.g., by washing or irrigating the surgical site and/or the cells.

As used herein, binding agent refers to any reagent or the like that forms a specific bond with a receptor carried on a target moiety, e.g., an antibody or antibody fragment that binds to an epitope of a cancer cell, or an agent that targets a certain region or structure(s) of a cell. In a preferred embodiment of the invention, the binding agent is an antibody or antibody fragment that specifically binds to cancer cells. In a more preferred embodiment of the invention, the binding agent binds an epitope of an antigen of ovarian cancer, breast cancer, or gastrointestinal cancer.

As used herein, physiologically acceptable fluid refers to any fluid or additive suitable for combination with a composition containing a hypocrellin derivative. Typically these fluids are used as a diluent or carrier. Exemplary physiologically acceptable fluids include but are not limited to preservative solutions, saline solution, an isotonic (about 0.9%) saline solution, or about a 5% albumin solution or suspension. It is intended that the present invention is not to be limited by the type of physiologically acceptable fluid used. The composition may also include pharmaceutically acceptable carriers. Pharmaceutically accepted carriers include but are not limited to saline, sterile water, phosphate buffered saline, and the like. Other buffering agents, dispersing agents, and inert non-toxic substances suitable for delivery to a patient may be included in the compositions of the present invention. The compositions may be solutions, suspensions or any appropriate formulation suitable for administration, and are typically sterile and free of undesirable particulate matter. The compositions may be sterilized by conventional sterilization techniques.

The compounds of the present invention may also be used in conjunction with and conjugated to a number of other compounds, signaling agents, enhancers, and/or targeting agents. For example, a hypocrellin derivative of the present invention may be conjugated to an antibody, preferably a monoclonal antibody. In accordance with the present invention, the binding agent includes any DNA minor-groove targeting agent, such as lexitropsin or netropsin, preferably to enhance the targeting of the phototoxicity in the cell nucleus.

Suitable enhancers include but are not limited to pKa modifiers, hypoxic cell radiosensitizers, and bioreductively activated anti-neoplastic agents, such as mitomycin C (preferably to effect or potentiate the toxicity of the compound in hypoxic cells or microorganisms). Suitable signaling agents include but are not limited to markers of apoptotic cell death or necrotic cell death, or regulatory molecules endogenous to cell cycle control or delay, preferably to potentiate the phototoxicity of the compound(s) by induction of apoptotic or necrotic cell death, or by inhibition of the repair of any form of lethal or potentially lethal damage (PLD).

As noted above, an embodiment of the invention includes binding agent-hypocrellin conjugates (or immunoconjugates) and the therapeutic use of these conjugates. In accordance with the present invention, any method of linking a binding agent to a hypocrellin may be used. For example, it is well known how to link an antibody or an antibody fragment to a photosensitizer. For example, Goff, et al., *British Journal of Cancer*, 74:1194–1198 (1996) discloses the production of an immunoconjugate by incubating a photosensitizer with monoclonal antibody OC125, an antibody that specifically binds to the CA125 antigen associated with most ovarian cancers.

BEST MODE(S) FOR CARRYING OUT THE INVENTION

We further illustrated the present invention with the following examples:

EXAMPLE 1

150 mg Hypocrellin B (0.28 mmol) is dissolved in 100 mL fresh distilled benzene containing excessive cyclopentylamine and the resulting solution is stirred for 18 hours. The solvent is removed under reduced pressure. Chloroform is used to wash the residue for 3–4 times, and the chloroform layer is washed with water for 3–4 times. Chloroform is evaporated, then thin-layer chromatography (TLC) is used to purify the residue using 3:1:0.5 (V:V:V) cyclohexane-ethyl acetate-95% ethanol as eluent. TLC is repeated twice for further purification, the amino-substituted demethoxylated hypocrellin B is obtained.

Characteristic of the Product:

UV-vis spectra ($\lambda_{max}$): 466 nm, 577 nm, 641 nm;

IR spectra ($v_{max}$): 3419 cm$^{-1}$, 2922 cm$^{-1}$, 1680 cm$^{-1}$, 1608 cm$^{-1}$; $^1$HNMR ($\delta$): 6.32 (s), 6.80 (s), 3.08 (s), 2.55 (s), 1.79 (s), 1.91 (s), 4.01 (s), 4.08 (s), 4.24 (s), 1.86 (m), 1.68 (m), 1.49 (m), 1.00 (m), 16.07, 15.78 ppm;

Mass spectra (m/z): 583 (M+)

EXAMPLE 2

150 mg Hypocrellin B (0.28 mmol) is dissolved in 100 mL fresh distilled benzene containing excessive cyclohexylamine and the resulting solution is stirred for 16 hours. The solvent is removed under reduced pressure. Chloroform is used to wash the residue for 3–4 times, and the chloroform layer is washed with water for 3–4 times. Chloroform is evaporated, then thin-layer chromatography (TLC) is used to purify the residue using 3:1:0.5 (V:V:V) cyclohexane-ethyl acetate-95% ethanol as eluent. TLC is used twice for further purification, the amino-substituted demethoxylated hypocrellin B is obtained.

Characteristic of the Product:

UV-vis spectra ($\lambda_{max}$): 468 nm, 579 nm, 642 nm;

IR spectra ($v_{max}$): 3421 cm$^{-1}$, 2920 cm$^{-1}$, 1678 cm$^{-1}$, 1605 cm$^{-1}$; $^1$HNMR ($\delta$): 6.12 (s), 6.79 (s), 3.05 (s), 2.54 (s), 1.76 (s), 1.89 (s), 4.05 (s), 4.10 (s), 4.21 (s), 1.84 (m), 1.40 (m), 1.26 (m), 1.01 (m), 16.08, 15.79 ppm;

Mass spectra (m/z): 597 (M+)

EXAMPLE 3

150 mg Hypocrellin B (0.28 mmol) is dissolved in 100 mL fresh distilled pyridine containing excessive benzylamine and the resulting solution is stirred for 15 hours. The solvent is removed under reduced pressure. Chloroform is used to wash the residue for 3–4 times, and the chloroform layer is washed with water for 3–4 times. Chloroform is evaporated, then thin-layer chromatography (TLC) is used to purify the residue using 3:1:0.5 (V:V:V) with cyclohexane-ethyl acetate-95% ethanol as eluent. TLC is repeated twice for further purification, the amino-substituted demethoxylated hypocrellin B is obtained.

Characteristic of the Product:

UV-vis spectra ($\lambda_{max}$): 468 nm, 623 nm;

IR spectra ($v_{max}$): 3438 cm$^{-1}$, 2942 cm$^{-1}$, 1683 cm$^{-1}$, 1605 cm$^{-1}$; $^1$HNMR ($\delta$): 7.53 (m), 7.34 (m), 6.32 (s), 6.80 (s), 3.08 (s), 2.55 (s), 1.79 (s), 1.91 (s), 4.01 (s), 4.08 (s), 4.24 (s), 1.86 (m), 16.07, 15.78 ppm;

Mass spectra (m/z): 603 (M+)

EXAMPLE 4

150 mg Hypocrellin B (0.28 mmol) is dissolved in 100 mL fresh distilled pyridine containing excessive 3-pyridylmethylamine and the resulting solution is stirred for 21 hours. The solvent is removed under reduced pressure. Chloroform is used to wash the residue for 3–4 times, and the chloroform layer is washed with water for 3–4 times. Chloroform is evaporated, then thin-layer chromatography (TLC) is used to separate the residue using 3:1:0.5 (V:V:V) cyclohexane-ethyl acetate-95% ethanol as eluent. TLC is repeated twice for further purification, the amino-substituted demethoxylated hypocrellin B are obtained.

Characteristics of the Product:

UV-vis spectra ($\lambda_{max}$): 471 nm, 625 nm;

IR spectra ($v_{max}$): 3435 cm$^{-1}$, 2940 cm$^{-1}$, 1682 cm$^{-1}$, 1604 cm$^{-1}$, $^1$HNMR (a): 8.53 (s), 8.29 (d), 7.77 (m), 7.36 (d), 6.37 (s), 6.59 (s), 3.98 (s), 2.63 (s), 1.78 (s), 2.28 (s), 4.04 (s), 4.06 (s), 4.13 (s), 1.90 (m), 1.62 (m), 1.42 (m), 1.27 (m), 1.00 (m), 16.59, 16.80 ppm;

Mass spectra (m/z): 603 (M+)

EXAMPLE 5

150 mg Hypocrellin B (0.28 mmol) is dissolved in 100 mL fresh distilled benzene containing excessive 4-pyridyl-methylamine and the resulting solution is stirred for 21 hours. The solvent is removed under reduced pressure. Chloroform is used to wash the residue for 3–4 times, and the chloroform layer is washed with water for 3–4 times. Chloroform is evaporated, then thin-layer chromatography (TLC) is used to separate the residue using 3:1:0.5 (V:V:V) cyclohexane-ethyl acetate-95% ethanol as eluent. The TLC is repeated twice for further purification, amino-substituted demethoxylated hypocrellin B is obtained.

Characteristic of the Product:

UV-vis spectra ($\lambda_{max}$): 398 nm, 474 nm, 596 nm;

IR spectra ($v_{max}$): 3433 cm$^{-1}$, 2928 cm$^{-1}$, 1680 cm$^{-1}$, 1600 cm$^{-1}$; $^1$HNMR (6): 8.56 (s), 8.24 (d), 7.72 (m), 7.28 (m), 6.47 (s), 6.50 (s), 5.25 (s), 2.58 (s), 2.80 (s), 3.90 (s), 3.88 (s), 3.89 (s), 4.02 (t), 4.20 (t), −16.07 ppm;

Mass spectra (m/z): 603 (M$^+$)

EXAMPLE 6

Materials and Methods

Chemicals

Hypocrellin B (HB) was prepared by quantitative potassium hydroxide dehydration of hypocrellin A (HA) followed by neutralization with Ha, chloroform extraction, and recrystallization with benzene-petroleum ether, 2-butylamino-2-demethoxy-hypocrellin B (2-BA-2-DMHB) was prepared by reflux with n-butylamine in pyridine, neutralization, and chloroform extraction of HB. The product was subjected to 1% citric acid-silica gel thin-layer chromatography (TLC), using a 6:1:1 mixture of petroleum ether/ethyl acetate/ethanol (95%) as eluent, and three compounds were obtained. They were the target compound (rate of flow (Rr)=0.64) and two by-products (Rr=0.74 and 0:40 respectively), which were identified by satisfactory NMR, mass spectra and elemental analysis [12]. The target compound was further purified with TLC and the desired product, 2-BA-2-DMHB, was obtained in 54% yield. The purity or HB and 2-BA-2-DMHB was assessed by high-performance liquid chromatography and found to be higher than 95%. The chemical structure of 2-BA-2-DMHB is shown below and absorption spectra is shown in FIG. 1. Their absorption spectra parameters are shown in Table 1. The photosensitizers were kept in lyophilized form until the day of experiments, at which time they were dissolved in DMSO.

TABLE 1

Absorption spectral parameters of photosensitizers in chloroform

| Compound | $\lambda_{max}$ (nm) (log$_6$) |
|---|---|
| HB | 466 (4.06), 548 (3.70), 580 (3.52) |
| 2-BA-2-DMHB | 463 (4.06), 583 (4.09), 621 (4.10) |

5,5-Dimethyl-1-pyrroline-N-oxide (DMPO) and 9,10-diphenylanthracene (DPA) were purchased from Aldrich Chemical Co. USA. Dulbecco's modified minimum essential medium (DMEM), fetal bovine serum (FBS), ethidium bromide (EB) and tris-(hydroxymethyl) aminomethane (Tris) were purchased from Gibco-BRL (Grand Island) N.Y. USA). Proteinase K and sodium dodecyl sulfate (SDS) were obtained from Merck (Rahway. N.J., USA). Agarose was obtained from Promega (Madison. Wyo, USA) RNase A, dimethyl sulfoxide (DMSO), 3-(4,5-dimethylthiazol-2-yl)-2, 5-diphenyl-2H-tetrazolium bromide (MTT) and propidium iodide (PI) were from Sigma Chemical Co. (St. Lows, Mo. USA). Hoechst dye 33342 (HO342) was obtained from Molecular Probes (Eugene, Oreg.) USA). Other reagents are analytical grade.

Determination of Reactive Oxygen Species Yields

Singlet oxygen yields were determined as previously reported [4] by the DPA bleaching method. The electron spin resonance (ESR) measurement of, spin trapping of DMPO was used to determine the generation of O$_2$ by hypocrellins [13].

Cell Cultures

HeLa cells were maintained as monolayer culture in DMEM containing 5% FBS and antibiotics PS (80 U/ml penicillin and 100 µg/ml streptomycin) at 37° C. in a humidified 5% CO$_2$ incubator.

Distribution Ratio

The distribution ratio or the photosensitizer is defined as [Sen/g cells]/[Sen/ml medium]. The values were measured as described previously [14]. Exponentially growing cells were incubated in DMEM with HB for 15 min or with 2-BA-2-DMHB for 6 h at 37° C., ranging from 0 to 5 µM. Steady-state intracellular levels were achieved at these times. The cells were detached using 0.2% trypsin/0.5 mM EDTA solution in phosphate-buffered saline (PBS) and centrifuge-washed to remove unbound dyes. The washed pellets (2×10$^6$) were dispersed in 3 ml of 10 mM Triton X-100 detergent. These solutions were excited at 460 nm and the fluorescence emission spectra were acquired using Hitachi-F4500 fluorescence spectrophotometer. Fluorescence at 610 nm was determined, corrected for the fluorescence of control (drug-free) sample, and compared with a standard fluorescence-intensity curve prepared with HB and 2-BA-2-DMHB solutions of known concentration.

EXAMPLE 7

Sensitizer Localization

Cells growing on glass were incubated in DMEM with 4 µM HB for 15 min or with 4 µM 2-BA-2-DMHB for 6 h at 37° C. Fluorescence was visualized by Nikon FXA microscope to assess sites of sensitizer location (excitation=400–450 nm, emission=600–650 nm).

Incubation and Irradiation

Stock sensitizer-DMSO solutions were diluted with DMEM containing 1% FBS. The final concentration of DMSO did not exceed 1% (v/v), Exponentially growing HeLa cells in 75-cm$^2$ flasks (Costar, Cambridge, Mass., USA) were incubated with 2-BA-2-DMHB in the dark for 6 h or HB in the dark for 15 min at 37° C. The cells were detached using 0.2% trypsin/0.5 mM EDTA solution in PBS and centrifuge-washed to remove unbound dyes. The cells were then transferred to 35-mm dishes (Costar)) 1 ml inch dish containing 3×10s cells, and irradiated with different doses of light. The light source was a Red Light Treatment Instrument (Institute of Electronic Academia Sinica, China), Its total power output, more than 90% at 600–700 nm was 50 mW cm$^2$ at the position of the, samples, measured with BTY-8204 radiometer (Beijing Institute of Solar Energy, China). Immediately after irradiation, 2 ml DMEM containing 7.5% FBS was added to each dish. Then a portion of the cells was assessed for survival as follows and the rest were incubated in the medium until they could be checked for nucleus staining, DNA fragmentation and flow cytometry analysis.

Cell Survival Studies

Cell survival was estimated by the MTT assay [11,15,16]. PDT-treated cells were transferred into flat-bottomed 96-well plates (Costar) 100 μl in each well containing 1×104 cells and the cells were incubated at 37° C. in a. $CO_2$, incubator for 20 h. Viability was determined by adding 10 μl MTT (10 mg ml$^{-1}$) to each well, and the mixture was incubated for 4 h at 37° C. Culture medium was then replaced with dimethylsulfoxide to dissolve the formazan crystals. The plates were shaken at room temperature for 10 min and read immediately at 595 nm on a Bio-Rad model 3550 microplate reader (Richmond, Calif. USA). Samples were measured in 12 replicates and each experiment was repeated at least twice. Survival of PDT-treated cells was normalized against cells incubated with photosensitizer alone.

The dark toxicity characteristic of each compound was assessed separately following a similar procedure for cell exposure to graded doses of 1 m for 15 min or 2-BA-2-DMHB for 6 h. Precautions were taken to avoid exposure of the cells to light throughout the period when'the cells were exposed to, or contained, photosensitizers.

Photopotentiation is defined as the molar concentration ratio of the the compound required to achieved an $LD_{50}$ in vitro in the dark to that required to achieve an $LD_{50}$ with 24 J cm$^{-2}$ of red light in a MTT assay [8].

Identification of Apoptotic Nuclei

Treated and control cells were incubated in DMEM with 0.5% FBS for 24 h at 37° C., then collected by detachment and centrifugation and incubated in a growth medium (FBS free) containing 5 μM H0342 for 5 min at 37° C. Nuclear fragmentation was assessed by fluorescence microscopy using Nikon FxA microscope. The EX wavelength was 330–380 nm with EM monitored at 420–450 nm [14]. Nuclei of both live and dead cells exhibit fluorescence; apoptotic cells can be identified by the appearance of bright fluorescent regions of nuclear condensation or fragmentation (17).

DNA Electrophoresis

The DNA was extracted as described previously [18] with some modification. Cells (2×106) were detached with the use of 0.2% trypsin/0.5 mM EDTA solution washed with PBS and pelleted by centrifugation. The cell pellets were suspended in lysis buffer consisting of 0.5% sodium dodecyl sulfate (SDS), 2 mM EDTA, 100 mg/ml proteinase K, and SO mM Tris-HC buffer (pH 8.0). After 24 h lysis at 37° C., the DNA was extracted with an equal volume of water-saturated phenol/chloroform/isoamyl alcohol (25:24:1). The aqueous phase was collected and DNA was precipitated with 0.5 volume ammonium acetate and 2.5 volumes cold absolute ethanol, and stored overnight at −20° C. The DNA was dissolved in TE (0.5 M EDTA in 1 M Tris-HCl buffer, pH 8.0) and incubated with DNase-free RNase A (100 mg/ml) at 37° C. for 1 h. The samples were electrophoresed for 3 h at 60 V in 1.5% agarose gel containing 0.5 μg ml$^{-1}$ ethidium bromide and visualized by UV transillumination.

Flow Cytometric Detection of DNA Fragmentation

A propidium iodide (PI) staining technique was used to assess the status of cellular DNA [19]. Cells were washed twice with ice-cold PBS and then permeabilized and fixed in 80% ethanol at 4° C. for 24 h. Cells were washed twice with PBS and suspended in PBS with RNase A (100 mg/ml) and incubated at 37° C. for 30 min. At this point the PI solution (10 mg/ml in PBS) was added to the cells in RNase solution, and the incubation was continued for 30 min at 4° C. After that, the cells were analyzed by Epics XL flow cytometer (Coulter, USA). Results are expressed as the percentage of cells exhibiting subdiploid (<2 N) amounts of DNA relative to the total number of cells analyzed.

EXAMPLE 8

Results

Reactive Oxygen Species Yields

The singlet oxygen yields of HB (0.76) and 2-BA-2-DMHB (0.44) were determined by DPA bleaching method, and shown in Table 2.

TABLE 2

Quantum yields of photosensitizers in DMSO

| Compound | Quantum yields ($^1O_2$) | Relative quantum yields ($O_2^-$) |
|---|---|---|
| HB | 0.76 | 1 |
| 2-BA-2-DMHB | 0.44 | 2.7 |

DMPO spin-trapping ESR measurement was used here to verify the formation of superoxide anion radical generated by photosensitization of HB and 2-BA-2-DMHB. The results show that the ability pf $O_2^-$ generation by 2-BA-2-DMHB was higher than that by HB (Table 2).

Distribution Ratio and Localization

We observed a distribution ratio of 49.1±2.2 for HB and 107.2±4.3 for 2-BA-2-DMHB, using extra-cellular drug concentrations that were varied between 0 and 5 μM. These results indicated that the intra-cellular level of 2-BA-2-DMHB was approximately two fold as much as HB when equimolar levels of the drugs were used.

Figure 2:
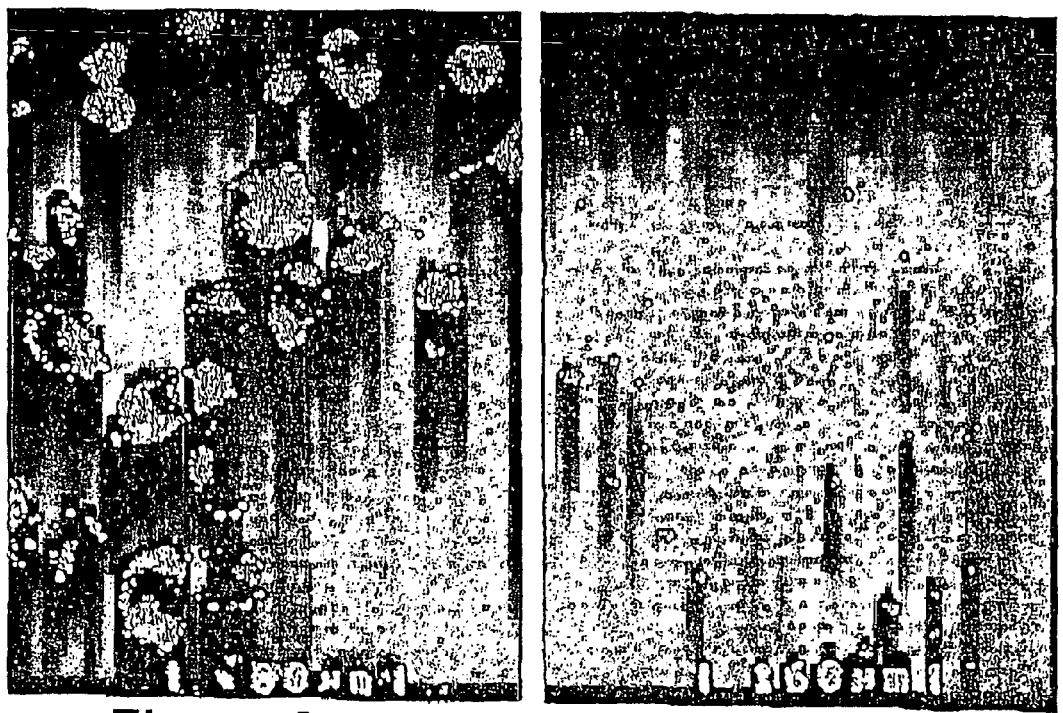
FIG. 2 shows the localization of HB (left) and 2-BA-2-DMHB (right).

Fluorescence microscopy indicated that for HB, prominent lysosomal uptake, and endoplasmic reticulum (ER) staining were evident, while the distribution of 2-BA-2-DMHB was primarily at ER (FIG. 2).

Photocytotoxicity and Lethal Dosage

Figure 3:
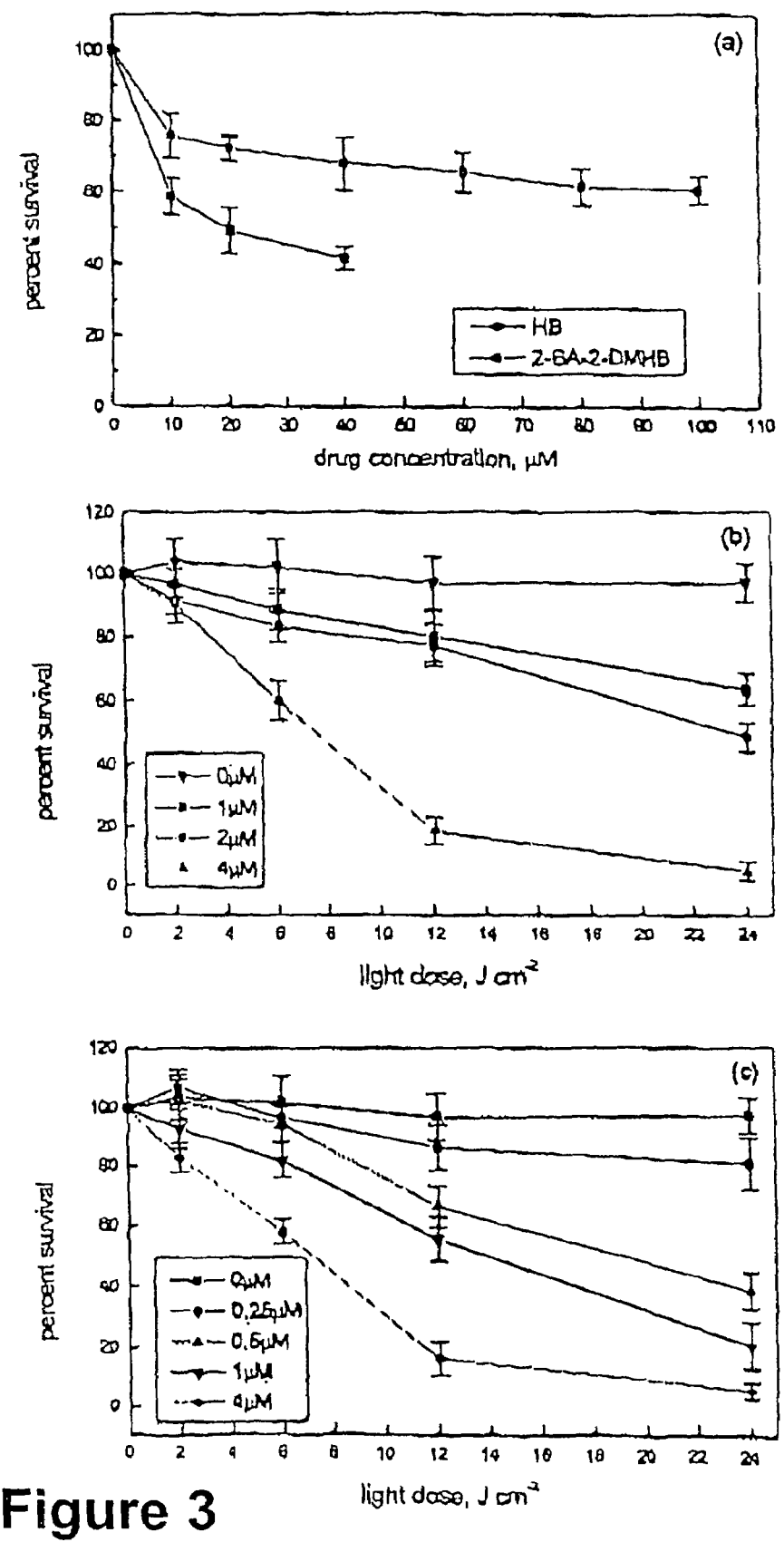
FIG. 3 shows the cytotoxicity (FIG. 3A) and phototoxicity (FIGS. #B and 3C, respectively) of HB and 2-BA-2-DMHB.

The doses of photosensitizer that exerted 50% cytotoxicity, $LD_{50}$ in the dark or light were estimated from the survival curves for each photosensitizer. Survival curves of the in vitro dark toxicity and phototoxicity of HB and 2-BA-2-DMHB are shown in FIG. 3. The $LD_{50}$ of HB in the dark was about 20 μM and that of 2-BA-2-DMHB was more than 100 KIM (FIG. 3a). Thus, 2-BA-2-DMHB has much lower cytotoxicity than HB.

No cytotoxicity was induced upon exposure of HeLa cells to red light alone (FIGS. 3b,c) and the corresponding MTT optical density was taken as 100% cell survival. In order to compare our results with Estey's results [8], we chose 24 J cm$^{-2}$ as the testing dose. At this light dose, the $LD_{50}$ of HB was about 2 μM and its photopotentiation factor was 10, which is equal to that of HB on EMT6 Ed mouse tumor cells [8]. However at this light dose, 2-BA-2-DMHB caused 50% cytotoxicity at a concentration within 0.25–0.5 FM (approx. 0.04 μM). Therefore 2-BA-2-DMHB was characterized by a more than 250-fold photopotentiation factor.

Hoechst 33342 Nuclear Staining

The morphology of dying cells was investigated using the nuclear staining Hoechst 33342. In the absence light irradiation, the nuclei of 2-BA-2-DMHB-treated HeLa cells remained intact, similar to those of the normal cells (FIG. 4a, b). However, apoptotic nuclei were detected in 2-BA-2-DMHB-photosensitized cells ($LD_{70}$) 24 h post-irradiation (FIG. 4c).

Gel Electrophoresis

Figure 5:
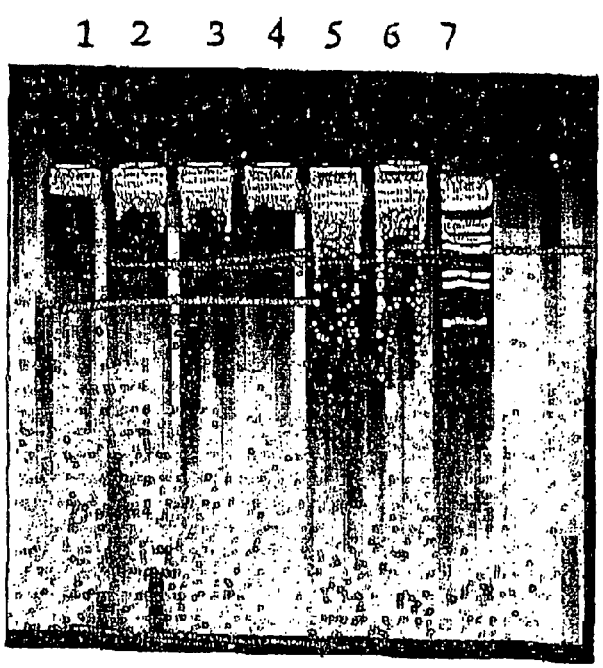
FIG. 5 shows the PDT-induced DNA Fragmentation in HeLa cells: lane 1, HB incubation alone (4 μM, 15 minutes); lanes 2 and 3, 24 hours after HB photosensitization at $LD_{70}$ and $LD_{90}$, respectively; lane 4, 2-BA-2-DMHB incubation alone (4 μM, 6 hours); lanes 5 and 6, 24 hours after 2-BA-2-DMHB photosensitization at $LD_{70}$ and $LD_{90}$, respectively; lane 7, marker (PUC-Mspl digest).

The fragmentation of DNA at the linker regions between nucleosomes yielding fragments that are multiplies of 180–200 base pairs in size is a typical hallmark of apoptosis. Agarose gel electrophoresis was used to examine the production of apoptotic DNA fragments. FIG. 5 shows the characteristic DNA ladder observed in HeLa cells 24 h subsequent being treated with HB and 2-BA-2-DMHB at $LD_{70}$ and $LD_{90}$, respectively (FIG. 5, lanes 2.3 and lanes 5,6). No DNA ladder was observed when cells were exposed to photosensitizers alone (FIG. 5, lanes 1 and 4). No obvious DNA ladder was detected at 3 and 6 h post-irradiation (data not shown).

Flow Cytometric Analysis

Figure 6:
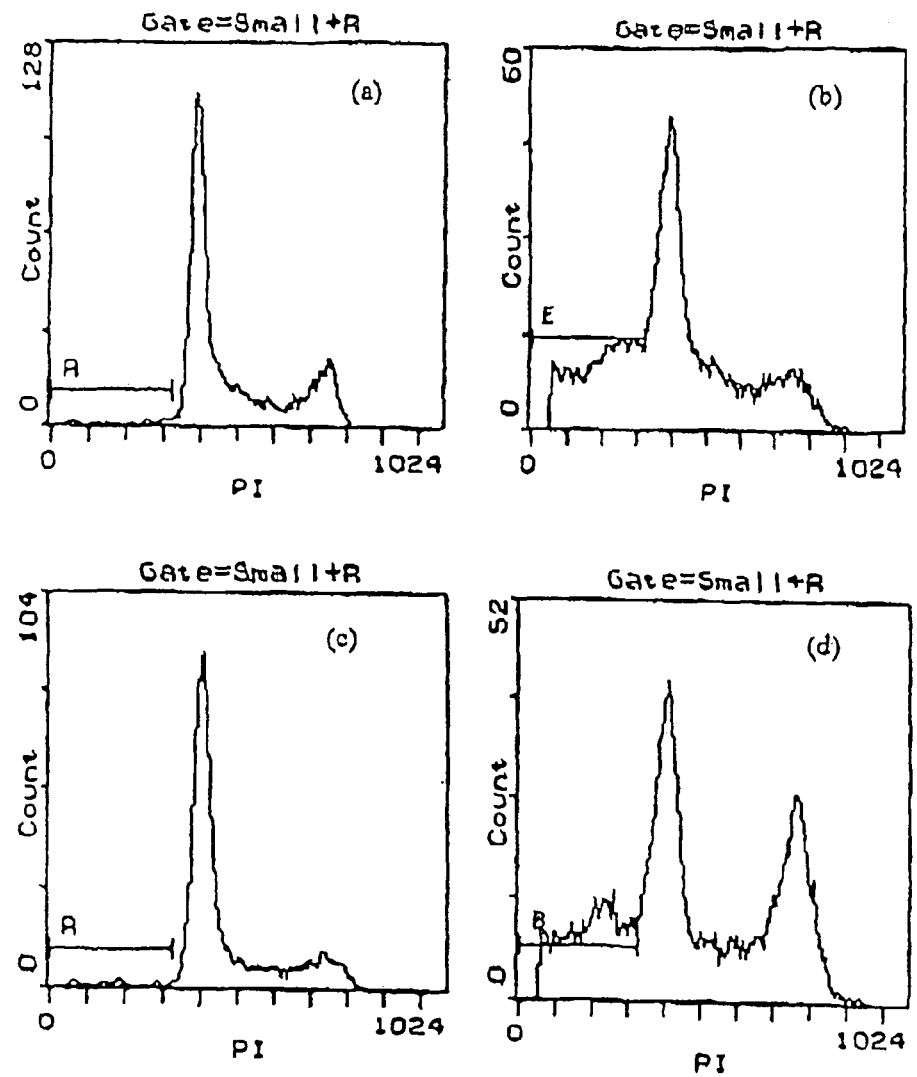
FIG. 6 shows the DNA histogram of HeLa cells treated with PDT.
Figure 7:
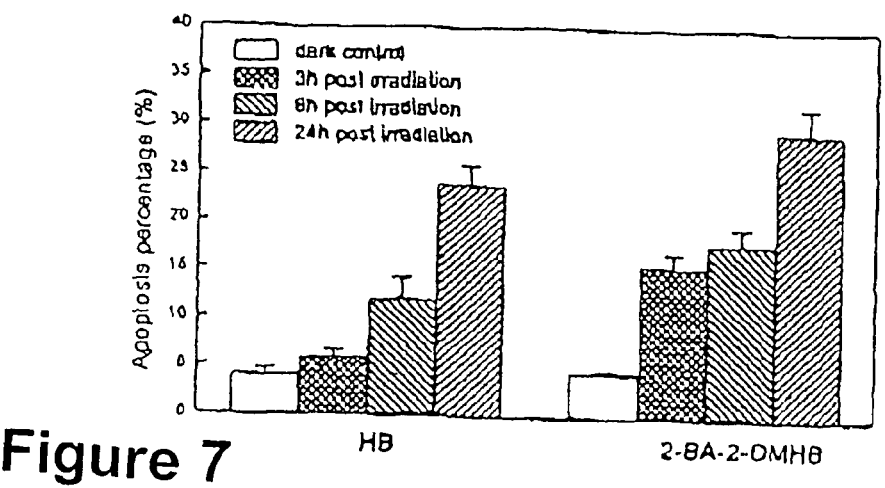
FIG. 7 shows the percentages of apoptic HeLa cells at different incubation times post-irradiation ($LD_{90}$).

The cells treated with HB and 2-BA-2-DMHB were analyzed by flow cytometry. The results showed the appearance of hypoploid cell population in photosensitized cells (FIG. 6). Percentages of apoptotic HeLa increased along with incubation time post-irradiation (FIG. 7). 2-BA-2-DMHB induced apoptosis more quickly than HB. It was also found that an obvious DNA ladder could be detected only when the percentage of apoptotic HeLa was more than 20%.

Results

Singlet oxygen is believed to be mainly responsible for cell death induced by photodynamic action [22,23]. However, it is interesting to note that the singlet oxygen yield (Table 2) was not strongly correlated with photopotentiation in this study. While the singlet oxygen yield of 2-BA-2-DMHB was more than half of that of HB, the $O_2^-$ yield of 2-BA-2-DMHD was 2.7 times as great as that of HB $O_2^-$ might play an important role in cell death induced by hypocrellin photosensitization. Furthermore, the intracellular level of 2-BA-2-DMHB was approximately two times as much as that of HB when equimolar levels of the drugs were used; this might be one of the reasons why 2-BA-2-DMHB had more excellent photosensitization than HB.

EXAMPLE 9

Figure 4:
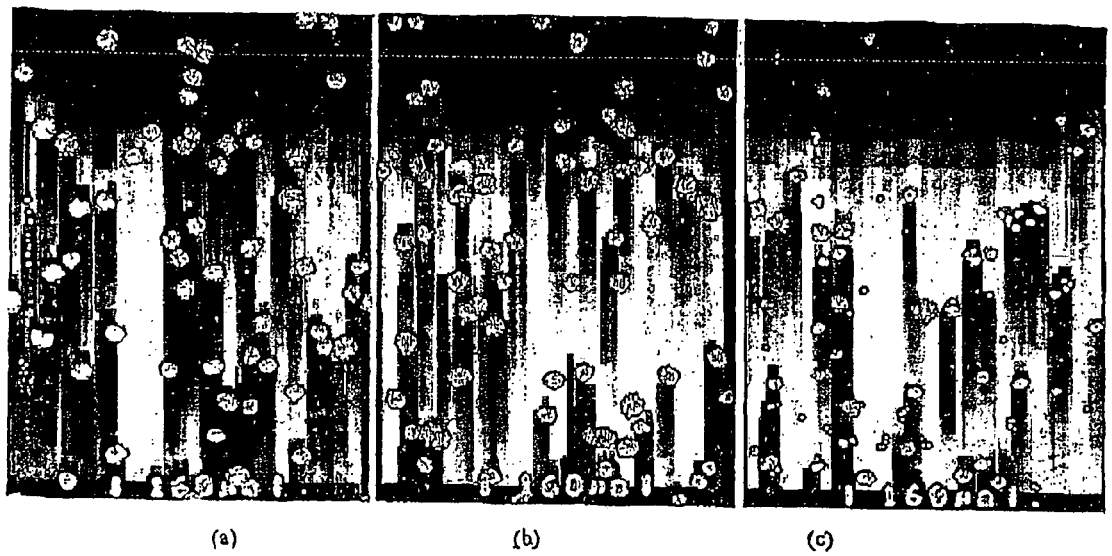
FIG. 4 shows fluorescence images of Hoechst 33342-stained HeLa cells. Cells were incubated in 4 μM 2-BA-2-DMHB for six hours and irradiated with $LD_{70}$.

The ability to induce a rapid apoptotic response is now believed to be important in the successful treatment of cancer by PDT [25]. The above examples demonstrate that HB and 2-BA-2-DMHB induced apoptosis in HeLa cells, as evidenced, by Hoechst 33342 nuclear staining, agarose gel electrophoresis and flow cytometric detection of DNA fragments (FIGS. 4–6). The percentages of apoptotic HeLa increased along with the incubation time post-irradiation. The typical DNA ladder was not obvious 3 and 6 h post-irradiation, but very clear 24 h post-irradiation, which suggested that DNA fragmentation was caused by an enzymatic process rather than by direct photochemical damage to DNA [11,26]. The examples also show that HB mainly localized at lysosomal and endoplasmic reticulum, and 2-BA-2-DMHB mainly localized at endoplasmic reticulum. Both endoplasmic reticulum and mitochondria are $Ca^{2+}$ pools in cells [27]. The reactive oxygen species in cells can damage the $Ca^{2+}$ transport systems located within ER and mitochondria, lead to a disruption of intracellular $Ca^{2+}$ homeostasis, and sustained $Ca^{2+}$ increases, resulting ultimately in apoptosis [28].

REFERENCES (1) T. J. Dougherty, Photodynamic therapy: part II, Semin. Surg. Oncol. tl (1995), 333–334.

(2) T. Reynolds, Photodynamic therapy expands its horizons, J. Natl. Cancer Inst. 89 (1997), 112–114.

(3) C. J. Gomer, Preclinical of first and second generation photosensitizers used in photodynamic therapy, Photochem. Photobiol. 54 (1991), 1093–1107.

(4) Z. J. Diwu, J. W. Lown, Photosensitization with anticancer agents 12, Perlyenequinoid pigments, a novel type of singlet oxygen sensitizer, J. Photochem. Photobiol. A: Chem. 64 (1992), 273–287.

(5) J. C. Yue, S. Z. Pang, M. H. Zhang, W. L. Xia, Photosensitized damage of ethanolamine-HB on murine ascitic hepatoma cells, Acta Biophys. Sin. 10 (1994), 485–492.

(6) S. Z. Pang, J. F. Qing, J. C. Yue, J. Y. An, Photosensitizing damage to morphology of HeLa cells by bromide of hypocrellin B (5-Br-HB), Acta Biophys. Sin. 10 (1994), 651–656.

(7) J. C. Yue, T. D. Wang, S. Z. Pang, J. Y. An, L. J. Jiang, Sulphonated hypocrellin B sensitized photodamage to ascitic hepatoma cells, J. Radiat. Res. Radiat. Process. 12 (1994), 100–104.

(8) E. P. Estcy, K. Brown, Z. J. Diwu, J. X. Liu, J. W. Lown, G. G. Miller, R. B. Moore, J. Tulip, M. S. Mcphee, Hypocrellins as photosensitizers for photodyamic therapy: a screening evaluation and pharmacokinetic study, Cancer Chemother. Pharmacol. 37 (1996), 343–350.

(9) Z. J. Diwu, R. P. Haugland, J. Liu, J. Lown, G. G. Miller, R. B. Moore, K. Brown, J. Tulip, M. S. Mcphee, Photosensitization by anticancer agents 21: new perylene- and amino-naphthoquinones, Free Radic. Bio. Med. 20 (1996), 589–593.

(10) G. G. Miller, K. Brown, A. M. Ballangrud, O. Barajas, Z. Xiao, J. Tulip, J. W. Lown, J. M. Leithoff, M. J. AllalunisTurner, R. D. Mehta, R. B. Moore, Preclinical assessment of hypocrellin B and hypocrellin B derivatives as sensitizers for photodynamic therapy of cancers: progress update, Photochem. Photobiol. 65 (1997), 714–722.

(11) W. G. Zhang, M. Weng, S. Z. Pang, M. H. Zhang, H. Y. Yang, H. X. Zhao, Z. Y. Zhang, A novel photosensitizer, 2-butylamino-2-demethoxy-hypocrellin A (2-BA-2-DMHA) 1. Synthesis of 2-BA-2-DMHA and its photo-toxicity to MGC803 cells, J. Photochem. Photobiol. B: Biol. 44 (1998), 21–28.

(12) T. Wu, S. J. Xu, J. Q. Shen, A. M. Song, S. Chen, M. H. Zhang, T. Shen, New potential photodynamic therapeutic anti-cancer agents: synthesis and characterization of demethoxy amino substituted hypocrellins, Anti-cancer Drug Design 15 (2000), 287–293.

(13) J. R. Harbour, M. L. Hair, Detection of superoxide ions in nonaqueous media generation by photolysis of pigment dispersion, J. Phys. Chem. 82 (1978), 1397–1399.

(14) Y Luo, D. Kessel, Initiation of apoptosis versus necrosis by photodynamic therapy with chloroaluminum phthalocyanine, Photochem. Photobiol. 66 (1997), 479–483.

(15) A. M. Richter, E. Waterfield, A. K. Jain, E. D. Stenberg, D. Dolphin, J. G. Levy, In vitro evaluation of phototoxic properties of four structurally related benzoporphyrin derivatives, Photochem. Photobiol. 52 (1990), 495–500.

(16) A. M. R. Fisher, K. Danerberg, D. Banerjee, J. R. Bertino, P. Danenberg, C. J. Gormer, Increased photosensitivity in HL60 cells expressing wild-type p53, Photochem. Photobiol. 66 (1997), 265–270.

(17) D. Kessel, Y. Luo, Delayed oxidative photodamage induced by photodynamic therapy, Photochem. Photobiol. 64 (1996), 601–604.

(18) D. Leszczynski, S. Fagerholm, K. Leszczynski, The effect of the broadband UVA radiation of myeloid leukemia cells: the possible role of protein kinase C in mediation of UVA-induced effects, Photochem. Photobiol. 64 (1996), 936–942.

(19) W. G. Telford, L. E. King, P. J. Fraker, Rapid quantitation of apoptosis in pure and heterogeneous cell populations using flow cytometry, J. Immunol. Methods 172 (1994), 1–16.

(20) B. C. Wilson, Photodynamic therapy: light delivery and dosage for second generation photosensitizers, in: G. Bock, S. Harnett (Eds.), Ciba Foundation Symposium 146: Photosensitizing Compounds: Their Chemistry, Biology and Clinical Use, Wiley, New York, 1989, pp. 61–73.

(21) E. Profio, A. R. Doiron, Transport of light in tissue in photodynamic therapy, Photochem. Photobiol. 46 (1987), 591–599.

(22) K. R. Weishaupt, C. J. Gomer, T. J. Dougherty, Identification of singlet oxygen as the cytotoxic agent in photoinactivation of a murine tumor, Cancer Res. 36 (1976), 2326–2329.

(23) C. J. Gomer, N. Rucker, A. Ferrario, S. Wong, Properties and applications of photodynamic therapy, Radiat. Res. 120 (1989), 1–18.

(24) M. L. Agarwal, M. E. Clay, E. J. Harvey, H. H. Evans, A. R. Antonez, N. L. Oleinick, Photodynamic therapy induces rapid cell death by apoptosis in L5178 lymphoma cells, Cancer Res. 51 (1991), 5993–5996.

(25) Y. Luo, C. K. Chang, D. Kessel, Rapid initiation of apoptosis by photodynamic therapy, Photochem. Photobiol. 63 (1996), 528–534.

(26) X. Y. He, R. A. Sikes, S. Thomsen, L. W. K. Chung, S. L. Jacques, Photodynamic therapy with photofrin II induces programmed cell death in carcinoma cell lines, Photochem. Photobiol. 59 (1994), 468–473.

(27) L. Missiaen, F. Wuytack, L. Raeymakers, H. De Smedt, G. Droogmans, I. Declerck, R. Casteels, $Ca^{2+}$ extrusion across plasma membrane and $Ca^{2+}$ uptake by intracellular stores, Pharmacol Ther. 50 (1991), 191–232.

(28) D. J. McConkey, S. Orrenius, The role of calcium in regulation of apoptosis, Biochem. Biophys. Res. Commun. 239 (1997), 357–366.

The invention claimed is:

1. A composition comprising at least one of an amino-substituted demethoxylated hypocrellin derivative according to the following structures:

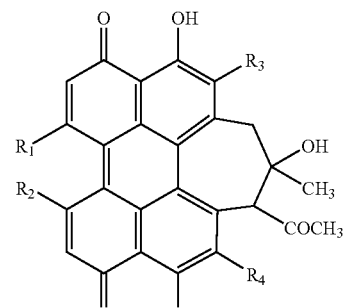

V

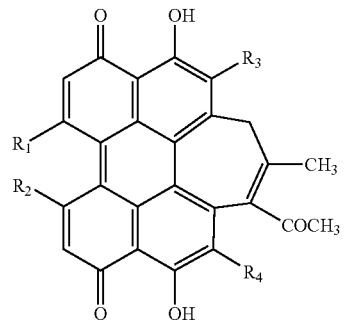

VI wherein $R_1$, $R_2$, $R_3$, $R_4$ are $OCH_3$, $NHCH_2Ar$, $NHCH(CH_2)_x$, or $NHCH(CH_2)_nAr$, with the proviso that at least one of $R_1$, $R_2$, $R_3$ and $R_4$ is $NHCH_2Ar$, $NHCH(CH_2)_x$ or $NHCH(CH_2)_nAr$, wherein Ar is a phenyl, naphthyl, pyridyl group, polycyclic aromatic group, or a heterocyclic moiety, and wherein $—CH(CH_2)_x$ is an alicyclic group, x=3, 4, 5, or 6 and n is 0–12.

2. The composition of claim 1 wherein $R_1$ and $R_2$, are $OCH_3$, and $R_3$ and $R_4$ are $OCH_3$, $NHCH_2Ar$, or $NHCH_2(CH_2)_nAr$, with the proviso that at least one of $R_3$ and $R_4$ is $NHCH_2Ar$, or $NHCH_2(CH_2)_nAr$.

3. The composition of claim 1, wherein $R_1$, $R_2$, $R_3$, and $R_4$ are $OCH_3$, $NHCH_2Ar$, or $NHCH(CH_2)_x$ with the proviso that at least one of $R_1$, $R_2$, $R_3$, or $R_4$ is $NHCH_2Ar$ or $NHCH(CH_2)_x$, wherein Ar is a phenyl or pyridyl group.

4. A method of producing a demethoxylated hypocrellin derivative of claim 1, comprising:
dissolving a hypocrellin in a solvent containing an aliphatic amine, and stirring the resulting solution;
removing the solvent, to produce a residue;
washing the residue; and
separating the residue.

5. The method of claim 4 wherein separating the residue comprises using thin-layer chromatography to separate the residue.

6. A method according to claim 4, wherein the hypocrellin is hypocrellin A or hypocrellin B.

7. A method according to claim 4, wherein the aliphatic amine is cyclopentylamine, cyclohexylamine, benzylamine, 3-pyridylmethylamine or 4-pyridylmethylamine.

8. A method according to claim 4, wherein the aliphatic amine is cyclobutylamine, histamine, 2-thiophenemethylamine, 2-pyrrolmethylamine, or tryptamine.

9. The method according to claim 4, wherein the solvent is benzene, pyridine, cyclohexane or 1,4-dioxane.

10. The method according to claim 4, wherein the solvent is chlorobenzene, toluene, hexanes, petroleum ether, tetrahydrofuran, or N,N-dimethylformamide.

11. A method of treatment comprising administering a demethoxylated hypocrellin derivative, and activating the demethoxylated hypocrellin derivative by exposing the demethoxylated hypocrellin derivative to light of a predetermined wavelength, wherein the hypocrellin derivative is an amino-substituted demethoxylated hypocrellin derivative comprising at least one of the following structures:

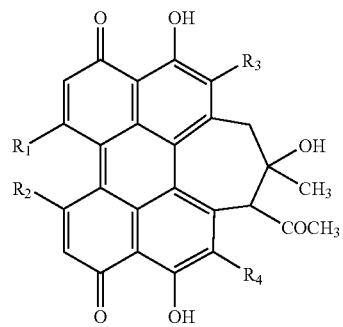

V

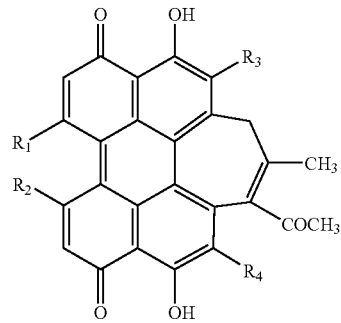

VI wherein $R_1$, $R_2$, $R_3$, $R_4$ are $OCH_3$, $NHCH_2Ar$, $NHCH(CH_2)_x$, or $NHCH(CH_2)_nAr$, with the proviso that at least one of $R_1$, $R_2$, $R_3$, or $R_4$ is $NHCH_2Ar$, $NHCH(CH_2)_x$, or $NHCH(CH_2)_nAr$ and wherein —$CH(CH_2)_x$ is an alicyclic group and x=3, 4, 5, or 6, and wherein Ar is a phenyl, pyridyl group, naphthyl, polycyclic aromatic, or a heterocyclic moiety, and n is 0–12.

12. The method of claim 11, wherein $R_1$, $R_2$, $R_3$, $R_4$ are $OCH_3$ or $NHCH_2(CH_2)Ar$, and Ar is a phenyl, naphthyl, polycyclic aromatic, or a heterocyclic moiety, and n is 0–12.

13. The method of claim 11, wherein $R_1$, $R_2$, $R_3$, and $R_4$ are $OCH_3$, $NHCH_2Ar$, or $NHCH(C_2)_x$, wherein Ar is a phenyl or pyridyl group, and wherein —$CH(CH_2)_x$ is an alicyclic group, and n is 3, 4, 5, or 6.

* * * * *